US007566542B2

(12) United States Patent
Pestlin et al.

(10) Patent No.: US 7,566,542 B2
(45) Date of Patent: Jul. 28, 2009

(54) USE OF PROTEIN ASC AS A MARKER FOR BREAST CANCER

(75) Inventors: Gabriele Pestlin, München (DE); Herbert Andres, Penzberg (DE); Peter Berndt, Basel (CH); Marie-Luise Hagmann, Penzberg (DE); Johann Karl, Peissenberg (DE); Hanno Langen, Steinen (DE); Werner Zolg, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/404,218

(22) Filed: Apr. 14, 2006

(65) Prior Publication Data

US 2006/0257952 A1 Nov. 16, 2006

Related U.S. Application Data

(63) Continuation of application No. PCT/EP2004/011597, filed on Oct. 15, 2004.

(30) Foreign Application Priority Data

Oct. 15, 2003 (EP) .................................. 03023507

(51) Int. Cl.
*G01N 33/53* (2006.01)
*G01N 33/574* (2006.01)
*G01N 33/48* (2006.01)
*G01N 33/536* (2006.01)
*G01N 33/537* (2006.01)
*G01N 33/577* (2006.01)

(52) U.S. Cl. ......................... 435/7.1; 435/7.23; 435/7.9; 435/7.91; 435/7.92; 435/7.93; 435/7.94; 435/7.95; 436/501; 436/518; 436/536; 436/64

(58) Field of Classification Search ................. 435/7.1, 435/7.21, 7.23, 7.91, 7.92, 7.93, 7.94, 7.95; 436/501, 503, 63, 64, 54, 518, 536; 530/387.1, 530/388.1, 388.22

See application file for complete search history.

(56) References Cited

U.S. PATENT DOCUMENTS 5,714,350 A * 2/1998 Co et al. ..................... 435/69.6
5,798,266 A * 8/1998 Quay et al. ................... 436/64
5,969,108 A * 10/1999 McCafferty et al. ........... 506/14
6,911,306 B1 * 6/2005 Vertino ............................ 435/6

FOREIGN PATENT DOCUMENTS

| WO | WO 00/60076 | 10/2000 |
| WO | WO 01/29235 A2 | 4/2001 |
| WO | WO 02/23200 A2 | 3/2002 |
| WO | WO 02/23200 A3 | 3/2002 |

OTHER PUBLICATIONS

Manor, D. et al. Cancer Research, 63: 4426-4433, Aug. 2003.*

Masumoto, J. et al., The Journal of Histochemistry & Cytochemistry, 49(10): 1269-1275, 2001.*

Levine, J. L., et al, Oncogene, 22: 3475-3488, May 2003.*

Walsh, M.D. et al., Breast Cancer Research and Treatment, 58: 255-266, 2000.*

Peterfy, F. et al, The Journal of Immunology, 130(4): 1809-1813, 1983.*

Bruck. C., Drebin, J., Glineur, C., Portetelle, D., "Purification of Mouse Monoclonal Antibodies from Ascitic Fluid by DEAE Affi-Gel Blue Chromatography", Methods in Enzymology, vol. 121, pp. 587-615, 1986.

Carney, P., Miglioretti, D., Yankaskas, B., Kerlikowske, K., Rosenberg, R., Rutter, C., Geller, B., Abraham, L., Taplin, S., Dignan, M., Cutter, G., "Individual and Combined Effects of Age, Breast Density, and Hormone Replacement Therapy Use on the Accuracy of Screening Mammography", Ann Intern Med., 2003; 138:168-175.

Chen, G., Gharib, G., Huang, C., Taylor, J., Misek, D., Kardia, S., Giordano, T., Iannettoni, M., Orringer, M., Hanash, S., Beer, D., "Discordant Protein and mRNA Expression in Lung Adenocarcinomas", Molecular & Cellular Proteomics 1.4, 2002, American Society for Biochemistry and Molecular Biology, Inc., pp. 304-313.

Conway, K., McConnell, B., Bowring, C., Donald, C., Warren, S., Vertino, P., "TMS1, a Novel Proapoptotic Caspase Recruitment Domain Protein, Is a Target of Methylation-induced Gene Silencing in Human Breast Cancers", Advances in Brief, Cancer Research 60, 6236-6242, Nov. 15, 2000.

Diamandis et al., eds. (1996) "Immunoassay", Academic Press, Boston.

Duffy, M., "Clinical Uses of Tumor Markers: A Critical Review", Critical Reviews in Clinical Laboratory Sciences, 38(3):224-262 (2001).

Esserman, L., Cowley, H., Eberle, C., Kirkpatrick, A., Chang, S., Berbaum, K., Gale, A., "Improving the Accuracy of Mammography: Volume and Outcome Relationships", Journal of the National Cancer Institute, vol. 94, No. 5, Mar. 6, 2002, pp. 369-375.

Galfre, G., Milstein, C., "Preparation of Monoclonal Antibodies: Strategies and Procedures", Methods in Enzymology, vol. 73, 1981, pp. 3-46.

Kuerer, H., Goldknopf, I., Fritsche, H., Krishnamurthy, S., Sheta, E., Hunt, K., "Identification of Distinct Protein Expression Patterns in Bilateral Matched Pair Breast Ductal Fluid Specimens from Women with Unilateral Invasive Breast Carcinoma", Cancer, vol. 95, No. 11, Dec. 1, 2002, pp. 2276-2282.

(Continued)

*Primary Examiner*—Alana M. Harris
*Assistant Examiner*—Anne L Holleran
(74) *Attorney, Agent, or Firm*—Marilyn L. Amick; Roche Diagnostics Operations, Inc.

(57) ABSTRACT

The present invention relates to the diagnosis of breast cancer. It discloses the use of protein ASC in the diagnosis of breast cancer. It relates to a method for diagnosis of breast cancer from a liquid sample, derived from an individual by measuring ASC in the sample. Measurement of ASC can, e.g., be used in the early detection or diagnosis of breast cancer.

7 Claims, 4 Drawing Sheets

OTHER PUBLICATIONS

Levine, J., Stimson-Crider, K., Vertino, P., "Effects of methylation on expression of TMS1/ASC in human breast cancer cells", Oncogene (2003) 22, 3475-3488.

Masumoto, J., Taniguchi, S., Ayukawa, K., Sarvotham, H., Kishino, T., Niikawa, N., Hidaka, E., Katsuyama, T., Higuchi, T., Sagara, J., "ASC, a Novel 22-κDa Protein, Aggregates during Apoptosis of Human Promyelocytic Leukemia HL-60-Cells", The Jouornal of Biological Chemistry, vol. 274, No. 48, Nov. 22, 1999, pp. 33835-33838.

Masumoto, J., Taniguchi, S., Nakayama, J., Shiohara, M., Hidaka, E., Katsuyama, T., Murase, S., Sagara, J., "Expression of Apoptosis-associated Speck-like Protein Containing a Caspase Recruitment Domain, a Pyrin N-terminal Homology Domain-containing Protein, in Normal Human Tissues", The Journal of Histochemistry & Cytochemistry, vol. 49(10); 1269-1275; 2001.

McConnell, B., Vertino, P., "Activation of a Caspase-9-mediated Apoptotic Pathway by Subcellular Redistribution of the Novel Caspase Recruitment Domain Protein TMS1", Cancer Research 60, 6243-6247, Nov. 15, 2000.

Moriai, R., Tsuji, N., Kobayashi, D., Yagihashi, A., Namiki, Y., Takahashi, H., Watanabe, N., "A Proapoptotic Caspase Recruitment Domain Protein Gene, TMS1, is Hypermethylated in Human Breast and Gastric Cancers", Anticancer Research 22: 4163-4168 (2002).

National Cancer Institute, Cancer Facts, Fact Sheet 5, 18 (1998) 1-5.

Shiohara, M. et al., Abstract#96, "ASC, Which is Composed of a Pyrin-N-Terminal Homology Domain and a Caspase-Recruitment Domain, Is Up-Regulated by Inflammation and Apoptosis in Human Neutrophils", Blood 98 (2001) 229a.

Singletary, S., Allred, C., Ashley, P., Bassett, L., Berry, D., Bland, K., Borgen, P., Clark, G., Edge, S., Hayes, D., Hughes, L., Hutter, R., Morrow, M., Page, D., Recht, A., Theriault, R., Thor, A., Weaver, D., Wieand, H., Greene, F., "Revision of the American Joint Committee on Cancer Staging System for Breast Cancer", Journal of Clinical Ongology, vol. 20, No. 17 (Sep. 1, 2002; pp. 3628-3636.

Studier, F., Rosenberg, A., Dunn, J., Dubendorff, J., "Use of T7 RNA Polymerase to Direct Expression of Cloned Genes", Methods in Enzymology, vol. 185, 1990, pp. 60-89.

Tijssen, P., "Practice and Theory on Enzyme Immunoassays", Elsevier, Amsterdam, 1990, pp. 43-78.

Untch, M., Sauer, H., Stieber, P., "Tumor Markers in Breast Cancer", J. Lab Med 001; 25 (9/10): 343-352.

Virmani, A., Rathi, A., Sugio, K., Sathyanarayana, G., Toyooka, S., Kischel, F., Tonk, V., Padar, A., Takahashi, T., Roth, J., Euhus, D., Minna, J., Gazdar, A., "Aberrant Methylation of TMS1 in Small Cell, Non Small Cell Lung Cancer and Breast Cancer", Int. J. Cancer: 106, 198-204 (2003).

Wulfkuhle, J., Sgroi, D., Krutzsch, H., McLean, K., McGarvey, K., Knowlton, M., Chen, S., Shu, H., Sahin, A., Kurek, R., Wallwiener, D., Merino, M., Petrocoin, E., Zhao, Y., Steeg, P., "Proteomics of Human Breast Ductal Carcinoma in Situ", Cancer Research 62, 6740-6749, Nov. 15, 2002.

Zhang, H., Liao, L., Kuang, S., Xu, J., "Spatial Distribution of the Messenger Ribonucleic Acid and Protein of the Nuclear Receptor Coactivator, Amplified in Breast Cancer-3, in Mice", Endocrinology 144(4): 1435-1443, 2003.

Zweig, M., Campbell, G., "Receiver-Operating Characteristic (ROC) Plots: A Fundamental Evaluation Tool in Clinical Medicine", Glin. Chem. 39/4, 561-577 (1993).

\* cited by examiner

USE OF PROTEIN ASC AS A MARKER FOR BREAST CANCER

RELATED APPLICATIONS

This application is a continuation of PCT/EP2004/011597 filed Oct. 15, 2004 and claims priority to European application EP 03023507.1 filed Oct. 15, 2003.

FIELD OF THE INVENTION

The present invention relates to the diagnosis of breast cancer. It discloses the use of apoptosis-associated speck-like protein containing a caspase-associated recruitment domain (ASC) in the diagnosis of breast cancer. Furthermore, it especially relates to a method for diagnosis of breast cancer from a liquid sample, derived from an individual by measuring ASC in said sample. Measurement of ASC can, e.g., be used in the early detection or diagnosis of breast cancer.

BACKGROUND OF THE INVENTION

Cancer remains a major public health challenge despite progress in detection and therapy. Amongst the various types of cancer, breast cancer (BC) is one of the most frequent cancers among women in the Western world.

The earlier cancer can be detected/diagnosed, the better is the overall survival rate. This is especially true for BC. The prognosis in advanced stages of tumor is poor. More than one third of the patients will die from progressive disease within five years after diagnosis, corresponding to a survival rate of about 40% for five years. Current treatment is only curing a fraction of the patients and clearly has the best effect on those patients diagnosed in an early stage of disease.

With regard to BC as a public health problem, it is essential that more effective screening and preventative measures for breast cancer will be developed.

The earliest detection procedures available at present for breast cancer involve using clinical breast examination and mammography. However, significant tumor size must typically exist before a tumor is palpable or can be detected by a mammogram. The densitiy of the breast tissue and the age are important predictors of the accuracy of screening mammography. The sensitivity ranges from 63% in women with extremely dense breasts to 87% in women with almost entirely fatty breasts. The sensitivity increases with age from 69% in women of about 40 years of age to 83% in women 80 years and older (Carney, P. A., et al., Ann. Intern. Med. 138 (3) (2003) 168-175). Only 20-25% of mammographically detected abnormalities that are biopsied prove to be malignant. The visualization of precancerous and cancerous lesions represents the best approach to early detection, but mammography is an expensive test that requires great care and expertise both to perform and in the interpretation of results (WHO, Screening for Breast Cancer, May 10, 2002; Esserman, L., et al., J. Natl. Cancer Inst. 94 (2002) 369-375).

In the recent years a tremendous amount of so-called breast specific or even so-called breast cancer specific genes has been reported. The vast majority of the corresponding research papers or patent applications are based on data obtained by analysis of RNA expression patterns in breast (cancer) tissue versus a different tissue or an adjacent normal tissue, respectively. Such approaches may be summarized as differential mRNA display techniques.

As an example for data available from mRNA-display techniques, WO 00/60076 shall be mentioned and discussed. This application describes and claims more than two hundred isolated polynucleotides and the corresponding polypeptides as such, as well as their use in the detection of BC. However, it is general knowledge that differences on the level of mRNA are not mirrored by the level of the corresponding proteins. A protein encoded by a rare mRNA may be found in very high amounts and a protein encoded by an abundant mRNA may nonetheless be hard to detect and find at all (Chen, G., et al., Molecular and Cellular Proteomics, 1.4 (2002) 304-313). This lack of correlation between mRNA-level and protein level is due to reasons like mRNA stability, efficiency of translation, stability of the protein, etc.

There also are recent approaches investigating the differences in protein patterns between different tissues or between healthy and diseased tissue in order to identify candidate marker molecules which might be used in the diagnosis of BC. Wulfkuhle et al. Cancer Research 62 (2002) 6740-6749 have identified fifty-seven proteins which were differentially expressed between BC tissue and adjacent normal tissue. No data from liquid samples obtained from an individual are reported.

WO 02/23200 reports about twelve breast cancer-associated spots as found by surface-enhanced laser desorption and ionization (SELDI). These spots are seen more frequently in sera obtained from patients with BC as compared to sera obtained from healthy controls. However, the identity of the molecule(s) comprised in such spot, e.g their sequence, is not known.

Nipple aspirate fluid (NAF) has been used for many years as a potential non-invasive method to identify breast cancer-specific markers. Kuerer et al. compared bilateral matched pair nipple aspirate fluids from women with unilateral invasive breast carcinoma by 2D gel electrophoresis (Kuerer, H. M., et al., Cancer 95 (2002) 2276-2282). 30 to 202 different protein spots were detected in the NAF of breasts suffering from breast carcinoma and not in the matched NAF of the healthy breasts. These spots were detected by a gel image analysis. But the identity of the protein spots is not known.

Despite the large and ever growing list of candidate protein markers in the field of BC, to date clinical/diagnostic utility of these molecules is not known. In order to be of clinical utility a new diagnostic marker as a single marker should be at least as good as the best single marker known in the art. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

At present, only diagnostic blood tests based on the detection of cancer antigen 15-3 (CA 15-3), a tumor-associated mucin, and carcinoembryonic antigen (CEA), a tumor associated glycoprotein, are available to assist diagnosis in the field of BC. CA 15-3 is usually increased in patients with advanced breast cancer. CA 15-3 levels are rarely elevated in women with early stage breast cancer (Duffy, M. J., Critical Reviews in Clinical Laboratory Sciences 38 (2001) 225-262). Cancers of the ovary, lung and prostate may also raise CA 15-3 levels. Elevated levels of CA 15-3 may be associated with non-cancerous conditions, such as benign breast or ovary disease, endometriosis, pelvic inflammatory disease, and hepatitis. Pregnancy and lactation can also cause CA 15-3 levels to raise (National Cancer Institute, Cancer Facts, Fact Sheet 5.18 (1998) 1-5). The primary use of CEA is in monitoring colon cancer, especially when the disease has metastasized. However, a variety of cancers can produce elevated levels of CEA, including breast cancer.

Due to the lack of organ and tumor specificity, neither measurement of CA 15-3 nor measurement of CEA are recommended for screening of BC. These tumor markers are helpful diagnostic tools in follow-up care of BC patients (Untch, M., et al., J. Lab. Med. 25 (2001) 343-352).

Whole blood, serum, plasma, or nipple aspirate fluid are the most widely used sources of sample in clinical routine. The identification of an early BC tumor marker that would allow reliable cancer detection or provide early prognostic information could lead to a diagnostic assay that would greatly aid in the diagnosis and in the management of this disease. Therefore, an urgent clinical need exists to improve the diagnosis of BC from blood. It is especially important to improve the early diagnosis of BC, since for patients diagnosed early on chances of survival are much higher as compared to those diagnosed at a progressed stage of disease.

It was the task of the present invention to investigate whether a new marker can be identified which may aid in BC diagnosis.

Surprisingly, it has been found that use of the marker ASC can at least partially overcome the problems known from the state of the art.

SUMMARY OF THE INVENTION

The present invention therefore relates to a method for the diagnosis of breast cancer comprising the steps of a) providing a liquid sample obtained from an individual, b) contacting said sample with a specific binding agent for ASC under conditions appropriate for formation of a complex between said binding agent and ASC, and c) correlating the amount of complex formed in (b) to the diagnosis of breast cancer Another preferred embodiment of the invention is a method for the diagnosis of breast cancer comprising the steps of a) contacting a liquid sample obtained from an individual with a specific binding agent for ASC under conditions appropriate for formation of a complex between said binding agent and ASC, and b) correlating the amount of complex formed in (a) to the diagnosis of breast cancer.

As the skilled artisan will appreciate, any such diagnosis is made in vitro. The patient sample is discarded afterwards. The patient sample is merely used for the in vitro diagnostic method of the invention and the material of the patient sample is not transferred back into the patient's body. Typically, the sample is a liquid sample.

DETAILED DESCRIPTION OF THE INVENTION

Figure 1:
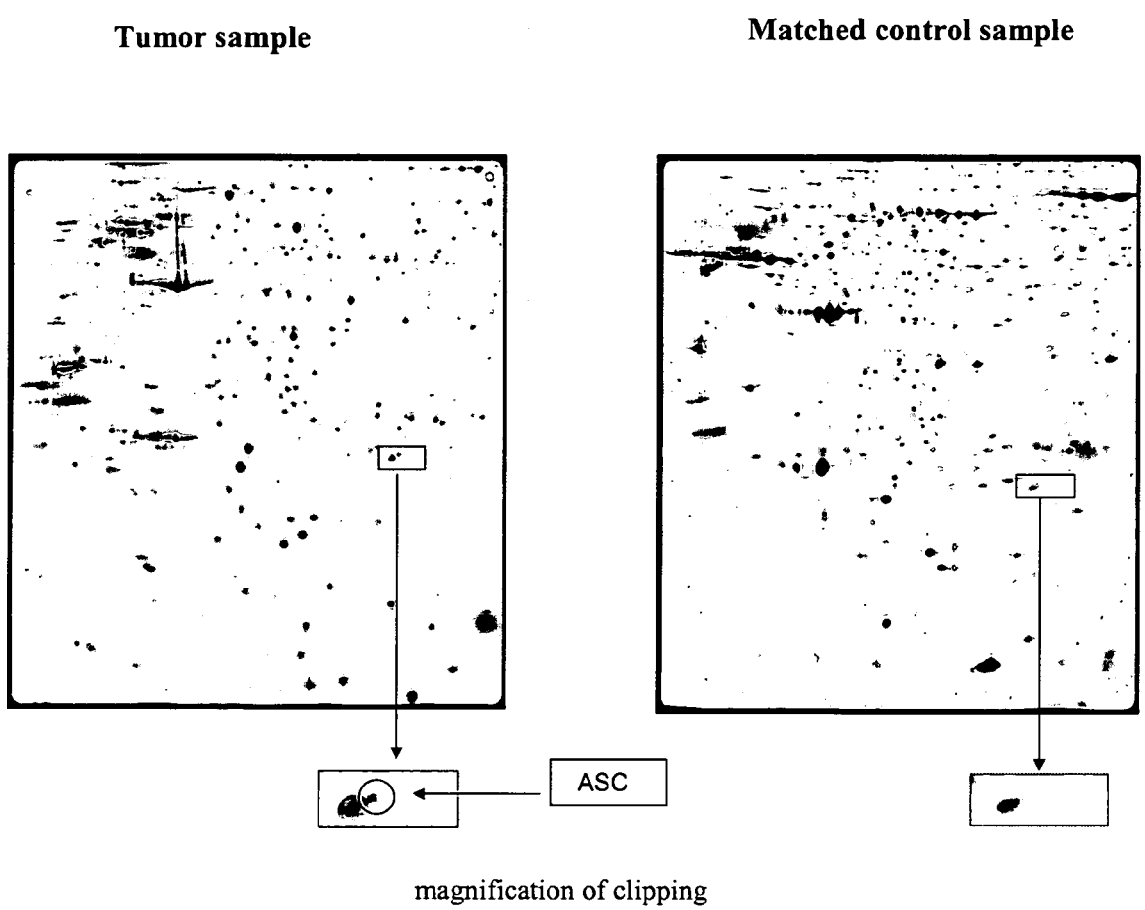
FIG. 1: The figure shows a typical example of a 2D-gel, loaded with a tumor sample (left side), and a gel, loaded with a matched control sample (right side). The circle in the enlarged section of these gels indicates the position for the protein ASC. Using the same method this protein has not been detected in healthy tissue. ASC migrates in the 2D gel corresponding to an isoelectric point of about pH 6 and an apparent molecular weight of about 22 kDa.
Figure 2:
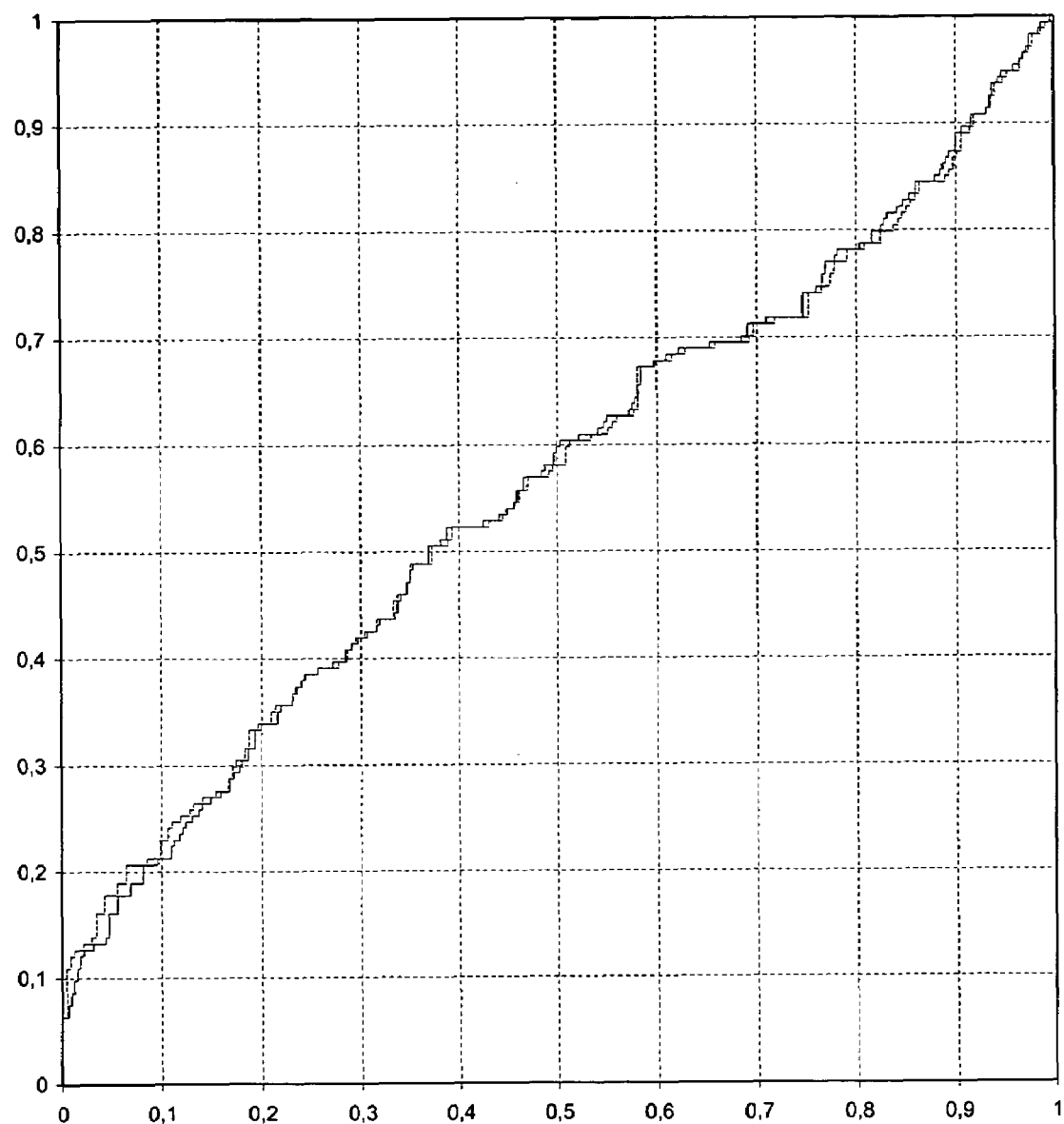
FIG. 2: The figure shows ROC-Curves for CA 15-3: Breast Cancer versus healthy controls (dotted line; ROC: 57%) and Breast Cancer versus healthy controls and disease controls (solid line; ROC: 57%). The x-axis indicates the value computed by subtracting from 1 the specificity value. The y-axis indicates sensitivity. In both the value of 1 corresponds to 100%. Breast cancer: 174 samples. Healthy controls: 234 samples. Disease controls: 86 samples.
Figure 3:
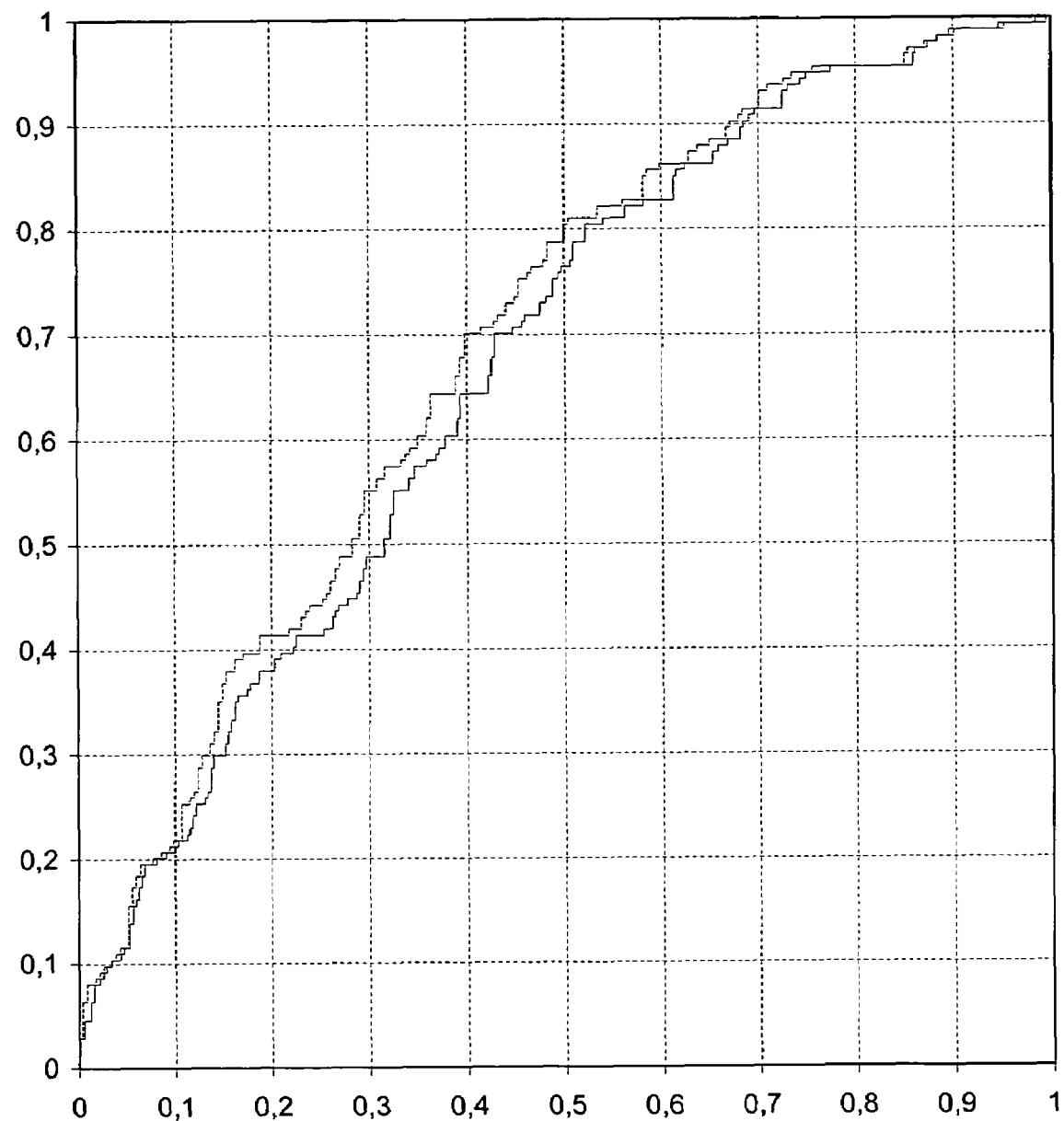
FIG. 3: The figure shows ROC-Curves for CEA: Breast Cancer versus healthy controls (dotted line; ROC: 69%) and Breast Cancer versus healthy controls and disease controls (solid line; ROC: 67%). The x-axis indicates the value computed by subtracting from 1 the specificity value. The y-axis indicates sensitivity. In both the value of 1 corresponds to 100%. Breast cancer: 174 samples. Healthy controls: 234 samples. Disease controls: 86 samples.
Figure 4:
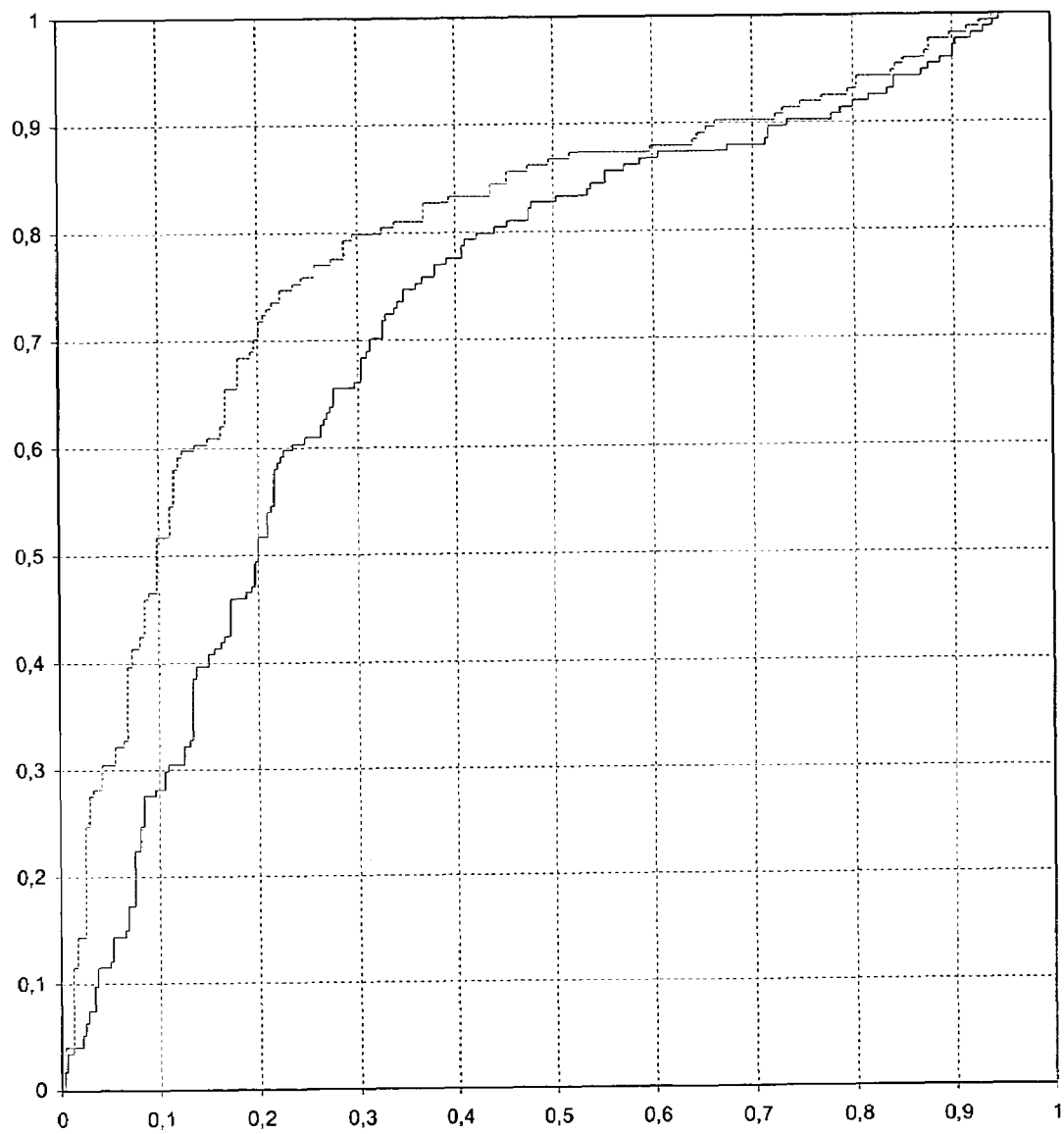
FIG. 4: The figure shows ROC-Curves for ASC: Breast Cancer versus healthy controls (dotted line; ROC: 80%) and Breast Cancer versus healthy controls and disease controls (solid line; ROC: 72%). The x-axis indicates the value computed by subtracting from 1 the specificity value. The y-axis indicates sensitivity. In both the value of 1 corresponds to 100%. Breast cancer: 174 samples. Healthy controls: 234 samples. Disease controls: 86 samples.

The "apoptosis-associated speck-like protein containing a caspase-associated recruitment domain" (ASC), also known as "target of methylation-induced silencing 1" (TMS1) (Swiss-PROT: Q9ULZ3) is characterized by the sequence given in SEQ ID NO: 1. This sequence translates to a theoretical molecular weight of 21,627 Da and to a theoretical isoelectric point of pH 6.29.

Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family.

By immunoscreening a promyelocytic cell line, Masumoto et al. isolated a cDNA encoding ASC. The deduced 195-amino acid protein contains an N-terminal pyrin-like domain (PYD) and an 87-residue C-terminal CARD. Western blot analysis showed expression of a 22-kDa protein and indicated that ASC may have proapoptotic activity by increasing the susceptibility of leukemia cell lines to apoptotic stimuli by anticancer drugs (Masumoto, J, et al., J. Biol. Chem. 274 (1999) 33835-33838).

Methylation-sensitive restriction PCR and methylation-specific PCR (MSP) analyses by Conway et al. indicated that silencing of ASC correlates with hypermethylation of the CpG island surrounding exon1 and that overexpression of DNMT1 (DNA cytosine-5-methyltransferase-1) promotes hypermethylation and silencing of ASC. Breast cancer cell lines, but not normal breast tissue, exhibited complete methylation of ASC and expressed no ASC message. Expression of ASC in breast cancer cell lines inhibited growth and reduced the number of surviving colonies. Conway et al. concluded that ASC functions in the promotion of caspase-dependent apoptosis and that overexpression of ASC inhibits the growth of breast cancer cells (Conway, K. E., et al., Cancer Research 60 (2000) 6236-6242).

McConnell and Vertino showed that inducible expression of ASC inhibits cellular prolifertion and induces DNA fragmentation that can be blocked by caspase inhibitor. Immunofluorescence microscopy demonstrated that induction of apoptosis causes a CARD-dependent shift from diffuse cytoplasmic expression to spherical perinuclear aggregates (McConnell, B. B., and Vertino, P. M., Cancer Research 60 (2000) 6243-6247).

Moriani et al. observed methylation of ASC gene not only in breast cancer cells but also in gastric cancer. They suggested a direct role for aberrant methylation of the ASC gene in the progression of breast and gastric cancer involving down-regulation of the proapoptotic ASC gene (Moriani, R., et al., Anticancer Research 22 (2002) 4163-4168).

Conway et al. examined primary breast tissues for TMS1 methylation and compared the results to methylation in healthy tissues (Conway K. E., et al., Cancer Research 60 (2000) 6236-6242). Levine et al. found that ASC silencing was not correlated with methylation of specific CpG sites, but rather was associated with dense methylation of ASC CpG island. Breast tumor cell lines containing exclusively methylated ASC copies do not express ASC, while in partially methylated cell lines the levels of ASC expression are directly related to the percentage of methylated ASC allels present in the cell population (Levine, J. J., et al., Oncogene 22 (2003) 3475-3488).

Virmani et al. examined the methylation status of ASC in lung cancer and breast cancer tissue. They found that aberrant methylation of ASC was present in 46% of breast cancer cell lines and in 32% of breast tumor tissue. Methylation was rare in non-malignant breast tissue (7%) (Virmani, A., et al., Int. J. Cancer 106 (2003) 198-204).

Shiohara et al. found out that up-regulation of ASC is closely associated with inflammation and apoptosis in human neutrophils (Shiohara, M., et al., Blood 98 (2001) 229a).

Masumoto et al. observed high levels of ASC abundantly expressed in epithelial cells and leucocytes (Masumoto, J., et al., Journal of Histochemistry and Cytochemistry 49 (2001) 1269-1275).

As obvious to the skilled artisan, the present invention shall not be construed to be limited to the full-length protein ASC of SEQ ID NO: 1. Physiological or artificial fragments of ASC, secondary modifications of ASC, as well as allelic variants of ASC are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO: 1. Such fragment may advantageously be used for generation of antibodies or as a standard in an immunoassay. More preferred the artificial fragment comprises at least two epitopes of interest appropriate for setting up a sandwich immunoassay.

In preferred embodiments, the novel marker ASC may be used for monitoring as well as for screening purposes.

When used in patient monitoring the diagnostic method according to the present invention may help to assess tumor load, efficacy of treatment and tumor recurrence in the follow-up of patients. Increased levels of ASC are directly correlated to tumor burden. After chemotherapy a short term (few hours to 14 days) increase in ASC may serve as an indicator of tumor cell death. In the follow-up of patients (from 3 months to 10 years) an increase of ASC can be used as an indicator for tumor recurrence.

In a preferred embodiment the diagnostic method according to the present invention is used for screening purposes. I.e., it is used to assess subjects without a prior diagnosis of BC by measuring the level of ASC and correlating the level measured to the presence or absence of BC.

The staging of cancer is the classification of the disease in terms of extent, progression, and severity. It groups cancer patients so that generalizations can be made about prognosis and the choice of therapy.

Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer) (Sobin, L. H., Wittekind, Ch. (eds): TNM Classification of Malignant Tumours, fifth edition, 1997). The staging system for breast cancer has recently been revised (Singletary, S. E., et al., Journal of Clinical Oncology 20 (2002) 3628-3636).

What is especially important is, that early diagnosis of BC translates to a much better prognosis. Therefore, best prognosis have those patients as early as in stage $T_{is}$, N0, M0 or T1-3; N0; M0, if treated properly have a more than 90% chance of survival 5 years after diagnosis as compared to a 5-years survival rate of only 18% for patients diagnosed when distant metastases are already present.

In the sense of the present invention early diagnosis of BC refers to a diagnosis at a pre-cancerous state (DCIS) or at a tumor stage where no metastases at all (neither proximal nor distal), i.e., $T_{is}$, N0, M0 or $T_1$-4; N0; M0 are present. $T_{is}$ denotes carcinoma in situ.

In a preferred embodiment ASC is used to diagnose BC in a non-metastatic stage, i.e., that diagnosis is made at stage $T_{is}$, N0, M0 or T1-3; N0; M0 (=$T_{is}$-3; N0; M0).

The diagnostic method according to the present invention is based on a liquid sample which is derived from an individual. Unlike to methods known from the art ASC is specifically measured from this liquid sample by use of a specific binding agent.

A specific binding agent is, e.g., a receptor for ASC, a lectin binding to ASC or an antibody to ASC. A specific binding agent has at least an affinity of $10^7$ l/mol for its corresponding target molecule. The specific binding agent preferably has an affinity of $10^8$ l/mol or even more preferred of $10^9$ l/mol for its target molecule. As the skilled artisan will appreciate the term specific is used to indicate that other biomolecules present in the sample do not significantly bind to with the binding agent specific for ASC. Preferably, the level of binding to a biomolecule other than the target molecule results in a binding affinity which is only 10%, more preferably only 5% of the affinity of the target molecule or less. A most preferred specific binding agent will fulfill both the above minimum criteria for affinity as well as for specificity.

A specific binding agent preferably is an antibody reactive with ASC. The term antibody refers to a polyclonal antibody, a monoclonal antibody, fragments of such antibodies, as well as to genetic constructs comprising the binding domain of an antibody. Any antibody fragment retaining the above criteria of a specific binding agent can also be used.

Antibodies are generated by state of the art procedures, e.g., as described in Tijssen (Tijssen, P., Practice and theory of enzyme immunoassays 11 (1990) the whole book, especially pages 43-78; Elsevier, Amsterdam). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108-115).

For the achievements as disclosed in the present invention monoclonal and polyclonal antibodies have been used. Polyclonal antibodies have been raised in rabbits. However, clearly also polyclonal antibodies from different species, e.g. rats or guinea pigs can also be used. Monoclonal antibodies have been produced using spleen cells from immunized mice. Since monoclonal antibodies can be produced in any amount required with constant properties, they represent ideal tools in development of an assay for clinical routine. The generation and use of monoclonal antibodies to ASC in a method according to the present invention is yet another preferred embodiment.

As the skilled artisan will appreciate now, that ASC has been identified as a marker which is useful in the diagnosis of BC, alternative ways may be used to reach a result comparable to the achievements of the present invention. For example, alternative strategies to generate antibodies may be used. Such strategies comprise amongst others the use of synthetic peptides, representing an epitope of ASC for immunization. Preferably, a synthetic peptide comprises a subsequence of SEQ ID NO: 1 which is specific for ASC, i.e., which has a comparatively low homology to other/related polypeptides. It is preferred that the synthetic peptide comprises a contiguous subsequence consisting of 5 to 25 amino acid residues of SEQ ID NO: 1. More preferred, the peptide comprises a contiguous subsequence consisting of 10 to 15 amino acid residues of SEQ ID NO: 1. Other strategies include the use of a SlyD-ASC fusion protein as described in Example 2 for immunization. Preferably, a fusion protein of the formula SlyD-(GGGS)$_5$-GGG-EGR-ASC-GGGS-HHH-HHH is used, whereby -(GGGS)$_5$-GGG is a first glycine-rich linker sequence, whereby IEGR is a Factor Xa cleavage site, whereby GGGS is a second glycine-rich linker sequence and HHHHHH is a His-tag.

Alternatively, DNA immunization also known as DNA vaccination may be used.

For measurement the liquid sample obtained from an individual is incubated with the specific binding agent for ASC under conditions appropriate for formation of a binding agent ASC-complex. Such conditions need not be specified, since the skilled artisan without any inventive effort can easily identify such appropriate incubation conditions.

As a final step according to the method disclosed in the present invention the amount of complex is measured and correlated to the diagnosis of BC. As the skilled artisan will appreciate there are numerous methods to measure the amount of specific binding agent ASC-complex all described in detail in relevant textbooks (cf., e.g., Tijssen P., supra, or Diamandis et al., eds. (1996) Immunoassay, Academic Press, Boston).

Preferably ASC is detected in a sandwich type assay format. In such assay a first specific binding agent is used to capture ASC on the one side and a second specific binding agent, which is labeled to be directly or indirectly detectable is used on the other side.

As mentioned above, it has surprisingly been found that ASC can be measured from a liquid sample obtained from an individual sample. No tissue and no biopsy sample is required to apply the marker ASC in the diagnosis of BC.

In a preferred embodiment the method according to the present invention is practiced with serum as liquid sample material.

In a further preferred embodiment the method according to the present invention is practiced with plasma as liquid sample material.

In a further preferred embodiment the method according to the present invention is practiced with whole blood as liquid sample material.

In a further preferred embodiment the method according to the present invention is practiced with nipple aspirate fluid as liquid sample material.

Whereas application of routine proteomics methods to tissue samples, leads to the identification of many potential marker candidates for the tissue selected, the inventors of the present invention have surprisingly been able to detect ASC in a bodily fluid sample. Even more surprising they have been able to demonstrate that the presence of ASC in such liquid sample obtained from an individual can be correlated to the diagnosis of breast cancer.

Antibodies to ASC with great advantage can be used in established procedures, e.g., to detect breast cancer cells in situ, in biopsies, or in immunohistological procedures.

Preferably, an antibody to ASC is used in a qualitative (ASC present or absent) or quantitative (ASC amount is determined) immunoassay.

Measuring the level of protein ASC has proven very advantageous in the field of BC. Therefore, in a further preferred embodiment, the present invention relates to use of protein ASC as a marker molecule in the diagnosis of breast cancer ASC from a liquid sample obtained from an individual.

The term marker molecule is used to indicate that an increased level of the analyte ASC as measured from a bodily fluid of an individual marks the presence of BC.

It is especially preferred to use the novel marker ASC in the early diagnosis of breast cancer.

The use of protein ASC itself, represents a significant progress to the challenging field of BC diagnosis. Combining measurements of ASC with other known markers, e.g. CA 15-3, CEA, cellular retinoic acid-binding protein II (Swiss-PROT: P29373) or with other markers of BC presently known or yet to be discovered, leads to further improvements. Therefore in a further preferred embodiment the present invention relates to the use of ASC as a marker molecule for breast cancer in combination with one or more marker molecules for breast cancer in the diagnosis of breast cancer from a liquid sample obtained from an individual. In this regard, the expression "one or more" denotes 1 to 10, preferably 1 to 5, more preferred 3. Preferred selected other BC markers with which the measurement of ASC may be combined are CEA, cellular retinoic acid-binding protein II (Swiss-PROT: P29373) and CA 15-3. Even more preferred, ASC is used as part of a marker panel at least comprising ASC and CA 15-3. Thus, a further preferred embodiment of the present invention is the use of the protein ASC as a marker molecule for breast cancer in combination with one or more marker molecules for breast cancer in the diagnosis of breast cancer from a liquid sample obtained from an individual, whereby the at least one other marker molecule is CA 15-3. Even more preferred, ASC is used as part of a marker panel at least comprising ASC, and cellular retinoic acid-binding protein II (Swiss-PROT: P29373). Thus, a further preferred embodiment of the present invention is the use of the protein ASC as a marker molecule for breast cancer in combination with one or more marker molecules for breast cancer in the diagnosis of breast cancer from a liquid sample obtained from an individual, whereby the at least one other marker molecule is cellular retinoic acid-binding protein II (Swiss-PROT: P29373). Even more preferred, ASC is used as part of a marker panel at least comprising ASC, cellular retinoic acid-binding protein II (Swiss-PROT: P29373) and CA 15-3. Thus, a further preferred embodiment of the present invention is the use of the protein ASC as a marker molecule for breast cancer in combination with two or more marker molecules for breast cancer in the diagnosis of breast cancer from a liquid sample obtained from an individual, whereby the at least two other marker molecules are cellular retinoic acid-binding protein II (Swiss-PROT: P29373) and CA 15-3.

Preferably, the inventive method is used with samples of patients suspected of suffering from breast cancer. An individual suspected of suffering from breast cancer is an individual for which other types of cancers have been excluded. Other cancers include but are not limited to cancers of the colon, lung, stomach, ovary, and prostate. A preferred embodiment of the invention is therefore a method for the diagnosis of breast cancer comprising the steps of a) providing a liquid sample obtained from an individual suspected of suffering from breast cancer, b) contacting said sample with a specific binding agent for ASC under conditions appropriate for formation of a complex between said binding agent and ASC, and c) correlating the amount of complex formed in (b) to the diagnosis of breast cancer.

Diagnostic reagents in the field of specific binding assays, like immunoassays, usually are best provided in the form of a kit, which comprises the specific binding agent and the auxiliary reagents required to perform the assay. The present invention therefore also relates to an immunological kit comprising at least one specific binding agent for ASC and auxiliary reagents for measurement of ASC. Also preferred is an immunological kit comprising at least one specific binding agent for ASC, at least one specific binding agent for CA 15-3 and auxiliary reagents for measurement of ASC and CA 15-3. Also preferred is an immunological kit comprising at least one specific binding agent for ASC, at least one specific binding agent for cellular retinoic acid-binding protein II (Swiss-PROT: P29373) and auxiliary reagents for measurement of ASC and cellular retinoic acid-binding protein II (Swiss-PROT: P29373). Also preferred is an immunological kit comprising at least one specific binding agent for ASC, at least one specific binding agent for cellular retinoic acid-binding protein II (Swiss-PROT: P29373), at least one specific binding agent for CA 15-3 and auxiliary reagents for measurement of ASC, CA 15-3 and cellular retinoic acid-binding protein II (Swiss-PROT: P29373).

Accuracy of a test is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results) (number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of the novel marker ASC has been assessed in comparison to and in combination with the established marker CA 15-3 using a receiver operator curve analysis (ROC; Zweig, M. H., and Campbell, G., Clin. Chem. 39 (1993) 561-577). This analysis has been based on well-defined patient cohorts consisting of 50 samples each from patients with invasive ductal or lobular carcinoma in T1-3; N0; M0, more progressed tumor, i.e., T4 and/or various severity of metastasis (N+ and/or M+), medullary, papillary, mucinous and tubular carcinoma, ductal carcinoma in situ, and healthy controls, respectively.

The following examples, references, sequence listing and figure are provided to aid the understanding of the present invention, the true scope of which is set forth in the appended claims. It is understood that modifications can be made in the procedures set forth without departing from the spirit of the invention.

Abbreviations

ABTS 2,2'-Azino-di-[3-ethylbenzthiazoline sulfonate (6)]diammonium salt

BSA bovine serum albumin cDNA complementary DNA

CHAPS (3-[(3-Cholamidopropyl)-dimethylammonio]-1-propane-sulfonate)

DMSO dimethyl sulfoxide

DTT dithiothreitol

EDTA ethylene diamine tetraacetic acid

ELISA enzyme-linked immunosorbent assay

HRP horseradish peroxidase

IAA iodacetamid

IgG immunoglobulin G

IEF isoelectric focussing

IPG immobilized pH gradient

LDS lithium dodecyl sulfate

MALDI-TOF matrix-assisted laser desorption/ionisation-time of flight mass spectrometry MES mesityl, 2,4,6-trimethylphenyl OD optical density PAGE polyacrylamide gel electrophoresis PBS phosphate buffered saline PI isoelectric point RTS rapid translation system SDS sodium dodecyl sulfate UICC International Union Against Cancer

SPECIFIC EMBODIMENTS

Example 1

Identification of ASC as a Potential Breast Cancer Marker

Sources of Tissue

In order to identify tumor-specific proteins as potential diagnostic markers for breast cancer, analysis of two different kinds of tissue is performed using proteomics methods.

In total, tissue specimen from 14 patients suffering from breast cancer are analyzed. From each patient two different tissue types are collected from therapeutic resections: Tumor tissue (>80% tumor) (T), and adjacent healthy tissue (N). The latter tissue type serves as matched healthy control sample. Tissues are immediately snap frozen after resection and stored at −80° C. before processing. Tumors are diagnosed by histopathological criteria.

Tissue Preparation 0.8-1.2 g of frozen tissue are put into a mortar and completely frozen by liquid nitrogen. The tissue is pulverized in the mortar, dissolved in the 10-fold volume (w/v) of lysis buffer (40 mM Na-citrate, 5 mM $MgCl_2$, 1% Genapol X-080, 0.02% Na-azide, Complete® EDTA-free [Roche Diagnostics GmbH, Mannheim, Germany, Cat. No. 1 873 580]) and subsequently homogenized in a Wheaton® glass homogenizer (20× loose fitting, 20× tight fitting). 3 ml of the homogenate are subjected to a sucrose-density centrifugation (10-60% sucrose) for 1 h at 4,500×g. After this centrifugation step three fractions are obtained. The fraction on top of the gradient contains the soluble proteins and is used for further analysis.

Immobilization of Monoclonal Antibody Anti-Human Albumin on CNBr-Activated Sepharose 4B Freeze-dried CNBr-activated Sepharose 4B (Amersham Biosciences, 17-0430-01) is reswollen and washed according to the instructions of the manufacturer. Monoclonal antibody directed against human albumin is dissolved in 0.1 M $NaHCO_3$, pH 8.3, 0.5 M NaCl, 10 mg/ml. 1 ml antibody solution is mixed with 1 ml reswollen CNBr-activated Sepharose 4B. The reaction time is 1 h. Blocking of the remaining active groups and washing of the gel is carried out according to the instructions of the manufacturer.

Depletion of Serum Albumin 7 ml anti-albumin gel is equilibrated in lysis buffer without Genapol X-080. 7 ml of the upper fraction of the sucrose-density centrifugation (see above, tissue preparation) are applied onto the column and washed through with lysis buffer without Genalpol X-080. The combined effluent is used for the isoelectric focussing experiments.

Isoelectric Focussing (IEF) and SDS-PAGE

For IEF, 3 ml of the HSA-depleted tissue preparation are mixed with 12 ml sample buffer (7 M urea, 2 M thiourea, 2% CHAPS, 0.4% IPG buffer pH 4-7, 0.5% DTT) and incubated for 1 h. The samples are concentrated in an Amicon® Ultra-15 device (Millipore GmbH, Schwalbach, Germany) and the protein concentration is determined using the Bio-Rad® protein assay (Cat. No. 500-0006; Bio-Rad Laboratories GmbH, München, Germany) following the instructions of the supplier's manual. To a volume corresponding to 1.5 mg of protein sample buffer is added to a final volume of 350 μl. This solution is used to rehydrate IPG strips pH 4-7 (Amersham Biosciences, Freiburg, Germany) overnight. The IEF is performed using the following gradient protocol: (1.) 1 minute to 500 V; (2.) 2 h to 3500 V; (3.) 22 h at constant 3500 V giving rise to 82 kVh. After IEF, strips are stored at −80° C. or directly used for SDS-PAGE.

Prior to SDS-PAGE the strips are incubated in equilibration buffer (6 M urea, 50 mM Tris/HCl, pH 8.8, 30% glycerol, 2% SDS), for reduction DTT (15 min, +50 mg DTT/10 ml), and for alkylation IAA (15 min, +235 mg iodacetamide/10 ml) is added. The strips are put on 12.5% polyacrylamide gels and subjected to electrophoresis at 1 W/gel and thereafter 1 h at 17 W/gel. Subsequently, the gels are fixed (50% methanol, 10% acetate) and stained overnight with Novex™ Colloidal Blue Staining Kit (Invitrogen, Karlsruhe, Germany, Cat No. LC6025, 45-7101)

Detection of ASC as a Potential Marker for Breast Cancer

Each patient is analyzed separately by image analysis with the ProteomeWeaver® software (Definiens AG, Germany, München). In addition, all spots of the gel are excised by a picking robot and the proteins present in the spots are identified by MALDI-TOF mass spectrometry (Ultraflex™ Tof/Tof, Bruker Daltonik GmbH, Bremen, Germany). For each patient, 4 gels from the tumor sample are compared with 4 gels each from adjacent tissue and analyzed for distinctive spots corresponding to differentially expressed proteins. By this means, protein ASC is found to be specifically expressed or strongly overexpressed in tumor tissue and not detectable in healthy control tissue. It therefore—amongst many other proteins—qualifies as a candidate marker for use in the diagnosis of breast cancer.

Example 2

Generation of Antibodies to the Breast Cancer Marker Protein ASC

Polyclonal antibody to the breast cancer marker protein ASC is generated for further use of the antibody in the measurement of serum and plasma and blood levels of ASC by immunodetection assays, e.g. Western Blotting and ELISA Recombinant Protein Expression and Purification In order to generate antibodies to ASC, recombinant expression of the protein is performed for obtaining immunogens. The expression is done applying a combination of the RTS 100 expression system and *E. coli*. In a first step, the DNA sequence is analyzed and recommendations for high yield cDNA silent mutational variants and respective PCR-primer sequences are obtained using the "ProteoExpert RTS *E. coli* HY" system. This is a commercial web-based service (www.proteoexpert.com). Using the recommended primer pairs, the "RTS 100 *E. coli* Linear Template Generation Set, His-tag" (Roche Diagnostics GmbH, Mannheim, Germany, Cat. No. 3186237) system to generate linear PCR templates from the cDNA for in-vitro transcription and expression of the nucleotide sequence coding for the ASC protein is used. For Western-blot detection and later purification, the expressed protein contains a His-tag. The best expressing variant is identified. All steps from PCR to expression and detection are carried out according to the instructions of the manufacturer. The respective PCR product, containing all necessary T7 regulatory regions (promoter, ribosomal binding site and T7 terminator) is cloned into the pBAD TOPO® vector (Invitrogen, Karlsruhe, Germany, Cat. No. K 4300/01) following the manufacturer's instructions. For expression using the T7 regulatory sequences, the construct is transformed into *E. coli* BL 21 (DE 3) (Studier, F. W., et al., Methods Enzymol. 185 (1990) 60-89) and the transformed bacteria are cultivated in a 1 l batch for protein expression.

Purification of His-ASC fusion protein is done following standard procedures on a Ni-chelate column. Briefly, 1 l of bacteria culture containing the expression vector for the His-ASC fusion protein is pelleted by centrifugation. The cell pellet is resuspended in lysis buffer, containing phosphate, pH 8.0, 7 M guanidium chloride, imidazole and thioglycerole, followed by homogenization using a Ultra-Turrax®. Insoluble material is pelleted by high speed centrifugation and the supernatant is applied to a Ni-chelate chromatographic column. The column is washed with several bed volumes of lysis buffer followed by washes with buffer, containing phosphate, pH 8.0 and urea. Finally, bound antigen is eluted using a phosphate buffer containing SDS under acid conditions.

Synthesis of Hemocyanin-Peptide-Conjugates for the Generation of Antibodies

Synthesis is carried out using heterobifunctional chemistry (maleimide/SH-chemistry). Selected cysteine containing ASC-peptides are coupled to 3-maleimidohexanoyl-N-hydroxysuccinimidester (MHS) activated hemocyanin from Concholepas concholepas (Sigma, B-8556).

Hemocyanin is brought to 10 mg/ml in 100 mM $NaH_2PO_4$/NaOH, pH 7.2. Per ml hemocyanin 100 µl MHS (12.3 mg in DMSO) are added and incubated for 1 h. The sample is dialyzed over night against 100 mM $NaH_2PO_4$/NaOH, pH 6.5 and adjusted to 6 mg/ml with dialysis buffer. A selected cysteine containing ASC-peptide was dissolved in DMSO (5 mg/ml for a peptide of 1500 Dalton). Per ml MHS-activated hemocyanin (6 mg/ml) 20 µl of 100 mM EDTA, pH 7.0 and 100 µl of the selected cysteine containing ASC-peptide are added. After 1 h the remaining maleimide groups are blocked by the addition of 10 µl 0.5 M cysteine/HCl per ml reaction mixture. This preparation is used for immunization without further purification.

Recombinant Fusion Protein Expression and Purification

In order to generate antibodies to ASC, recombinant expression of a SlyD-ASC fusion protein is performed to obtain immunogens. Therefore, an expression vector is constructed containing a gene encoding SlyD-(GGGS)$_5$-GGG-IEGR-ASC-GGGS-HHHHHH. For purification and Western blot detection, the construct contains a carboxyterminal His-Tag (HHHHHH). An additional GS-Linker ((GGGS)$_5$-GGG) and a cleavage site for Factor Xa (IEGR) is inserted between SlyD and ASC. Expression is done in *E. coli* under control of the T5-promoter.

In a first step, PCR is done using the vector pSO60 (pET24 carrying an expression cassette encoding SlyD-(GGGS)$_5$-GGG-SlyD) as a template. By use of primer 1 (SEQ ID NO:2) and primer 2 (SEQ ID NO:3), monoSlyD is obtained carrying an EcoRI-site and a ribosomal binding site at the 5'-end and a BamHI-site, the IEGR-encoding sequence and a SacI-site at the 3'-end, respectively. The generated PCR-product is cloned as a EcoRI/SacI-fragment into pQE80L (Qiagen, Hilden) giving pQE80-SlyD.

Secondly, ASC is amplified from pBC14 (pET24 carrying ASC) as the template. By use of primer 3 (SEQ ID NO:4) and primer 4 (SEQ ID NO:5), a BamHI-site and an IEGR-encoding sequence at the 5'-end as well as a GGGS-HHHHHH-encoding sequence and an additional HindIII-site at the 3'-end are inserted.

This PCR-product is cloned as a BamHI/HindIII fragment into pQE80-SlyD resulting in the final expression construct (pQE80-SlyD-ASC). All PCR- and cloning-steps are performed according to the manufacturer's instructions.

For expression under control of the T5 promoter, *E. coli* C600 cells (Stratagene, Heidelberg) are transformed with the final construct. Expression strains are cultivated in a 1 l batch for protein production.

Purification of His-SlyD-ASC fusion protein is done following standard procedures on a Ni-chelate column. Briefly, 1 liter of bacteria culture containing the expression vector for the SlyD-ASC-His-fusion protein is pelleted by centrifugation. The cell pellet is resuspended in lysis buffer containing Tris/HCl, pH 8, CHAPS, EDTA und lysozyme, followed by homogenization using a Ultra-Turrax®. DNA is enzymatically degraded by the addition of magnesium chloride and DNase. The inclusion bodies are pelleted by centrifugation. The pellet is dissolved in phosphate buffer, pH 8.0, 7 M guanidinium chloride and loaded on a Ni-chelate column. The column is washed with several bed volumes phosphate buffer, pH 8.0, 7 M guanidinium chloride. Then, the phosphate buffer, pH 8.0, 7 M guanidinium chloride is replaced by phosphate buffer, pH 8.0, NaCl to induce refolding of the matrix bound protein. The refolded fusion protein is eluted by phosphate buffer, pH 8.0, NaCl, imidazole.

Production of Monoclonal Antibodies Against ASC a) Immunization of Mice 12 week old A/J mice are initially immunized intraperitoneally with 100 µg ASC, fusion protein or hemocyanin-peptide-conjugate (see above). This is followed after 6 weeks by two further intraperitoneal immunizations at monthly intervals. In this process each mouse is administered 100 µg ASC or hemocyanin-peptide-conjugate adsorbed to aluminium hydroxide and $10^9$ germs of *Bordetella pertussis*. Subsequently the last two immunizations are carried out intravenously on the 3rd and 2nd day before fusion using 100 µg ASC or hemocyanin-peptide-conjugate in PBS buffer for each.

b) Fusion and Cloning

Spleen cells of the mice immunized according to a) are fused with myeloma cells according to Galfre, G., and Milstein, C., Methods in Enzymology 73 (1981) 346. In this process ca. $1 \times 10^8$ spleen cells of the immunized mouse are mixed with $2 \times 10^7$ myeloma cells (P3X63-Ag8-653, ATCC CRL1580) and centrifuged (10 min at 300×g and 4° C.). The cells are then washed once with RPMI 1640 medium without foetal calf serum (FCS) and centrifuged again at 400×g in a 50 ml conical tube. The supernatant is discarded, the cell sediment is gently loosened by tapping, 1 ml PEG (molecular weight 4000, Merck, Darmstadt) is added and mixed by pipetting. After 1 min in a water-bath at 37° C., 5 ml RPMI 1640 without FCS is added drop-wise at room temperature within a period of 4-5 min. Afterwards 5 ml RPMI 1640 containing 10% FCS is added drop-wise within ca. 1 min, mixed thoroughly, filled to 50 ml with medium (RPMI 1640+10% FCS) and subsequently centrifuged for 10 min at 400×g and 4° C. The sedimented cells are taken up in RPMI 1640 medium containing 10% FCS and sown in hypoxanthine-azaserine selection medium (100 mmol/l hypoxanthine, 1 µg/ml azaserine in RPMI 1640+10% FCS). Interleukin 6 at 100 U/ml is added to the medium as a growth factor.

After ca. 10 days the primary cultures are tested for specific antibody. ASC-positive primary cultures are cloned in 96-well cell culture plates by means of a fluorescence activated cell sorter. In this process again interleukin 6 at 100 U/ml is added to the medium as a growth additive.

c) Immunoglobulin Isolation from the Cell Culture Supernatants

The hybridoma cells obtained are sown at a density of $1\times10^5$ cells per ml in RPMI 1640 medium containing 10% FCS and proliferated for 7 days in a fermenter (Thermodux Co., Wertheim/Main, Model MCS-104XL, Order No. 144-050). On average concentrations of 100 μg monoclonal antibody per ml are obtained in the culture supernatant. Purification of this antibody from the culture supernatant is carried out by conventional methods in protein chemistry (e.g. according to Bruck, C., et al., Methods in Enzymology 121 (1986) 587-695).

Generation of Polyclonal Antibodies a) Immunization

For immunization, a fresh emulsion of the protein solution (100 μg/ml ASC, fusion protein or hemocyanin-peptide-conjugate) and complete Freund's adjuvant at the ratio of 1:1 is prepared. Each rabbit is immunized with 1 ml of the emulsion at days 1, 7, 14 and 30, 60 and 90. Blood is drawn and resulting anti-ASC serum used for further experiments as described in Examples 3 and 4.

b) Purification of IgG (Immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 μl /ml of diluted sample) is added drop-wise under vigorous stirring. After 30 min the sample is centrifuged (13,000×g, 30 min, 4° C.), the pellet discarded and the supernatant collected. The pH of the supernatant is adjusted to 7.5 by the addition of 2 M Tris-base and filtered (0.2 μm).

The immunoglobulin in the supernatant is precipitated under vigorous stirring by the drop-wise addition of a 4 M ammonium sulfate solution to a final concentration of 2 M. The precipitated immunoglobulins are collected by centrifugation (8,000×g, 15 min, 4° C.).

The supernatant is discarded. The pellet is dissolved in 10 mM $NaH_2PO_4$/NaOH, pH 7.5, 30 mM NaCl and exhaustively dialyzed. The dialysate is centrifuged (13,000×g, 15 min, 4° C.) and filtered (0.2 μm).

Biotinylation of Polyclonal Rabbit IgG

Polyclonal rabbit IgG is brought to 10 mg/ml in 10 mM $NaH_2PO_4$/NaOH, pH 7.5, 30 mM NaCl. Per ml IgG solution 50 μl Biotin-N-hydroxysuccinimide (3.6 mg/ml in DMSO) are added. After 30 min at room temperature, the sample is chromatographed on Superdex 200 (10 mM $NaH_2PO_4$/NaOH, pH 7.5, 30 mM NaCl). The fraction containing biotinylated IgG are collected. Monoclonal antibodies are biotinylated according to the same procedure.

Digoxygenylation of Polyclonal Rabbit IgG

Polyclonal rabbit IgG is brought to 10 mg/ml in 10 mM $NaH_2PO_4$/NaOH, 30 mM NaCl, pH 7.5. Per ml IgG solution 50 μl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on Superdex® 200 (10 mM $NaH_2PO_4$/NaOH, pH 7.5, 30 mM NaCl). The fractions containing digoxigenylated IgG are collected. Monoclonal antibodies are labeled with digoxigenin according to the same procedure.

Example 3

Western Blot for the Detection of ASC in Human Serum and Plasma Samples

SDS-PAGE and Western Blotting are carried out using reagents and equipment of Invitrogen, Karlsruhe, Germany. Human plasma samples are diluted 1:20 in reducing NuPAGE® (Invitrogen) LDS sample buffer and heated for 5 min at 95° C. 10 μl aliquots are run on 4-12% NuPAGE® gels (Bis-Tris) in the MES running buffer system. The gel-separated protein mixture is blotted onto nitrocellulose membranes using the Invitrogen XCell II™ Blot Module (Invitrogen) and the NuPAGE® transfer buffer system. The membranes are washed 3 times in PBS/0.05% Tween-20 and blocked with SuperBlock Blocking Buffer (Pierce Biotechnology, Inc., Rockford, Ill., USA). The biotinylated primary antibody is diluted in SuperBlock Blocking Buffer (0.01-0.2 μg/ml) and incubated with the membrane for 1 h. The membranes are washed 3 times in PBS/0.05% Tween-20. The specifically bound biotinylated primary antibody is labeled with a streptavidin-HRP-conjugate (20 $mU_{ABTS}$/ml in SuperBlock Blocking Buffer). After incubation for 1 h, the membranes are washed 3 times in PBS/0.05% Tween-20. The bound streptavidin-HRP-conjugate is detected using a chemiluminescent substrate (SuperSignal West Fernto Substrate, Pierce Biotechnology, Inc., Rockford, Ill., USA) and autoradiographic film. Exposure times varies from 10 min to over night.

Example 4

ELISA for the Measurement of ASC in Human Serum and Plasma Samples

For detection of ASC in human serum or plasma, a sandwich ELISA was developed using streptavidin-coated 96-well microtiter plates.

A 20 μl aliquot of a human serum or plasma sample or a serial dilution of the recombinant SlyD-ASC-His-fusion protein as standard antigen were incubated with 100 μl biotinylated polyclonal anti-ASC antibody (1 μg/ml) and with digoxygenylated polyclonal anti-ASC antibody (1 μg/ml) in 10 mM phosphate, pH 7.4, 1% BSA, 0.9% NaCl and 0.1% Tween-20. After incubation for 90 min at 30° C., the plates were washed three times with 0.9% NaCl, 0.1% Tween-20. For the detection of antigen-antibody complexes, 150 μl of an monoclonal anti-digoxigenin peroxidase conjugate in 10 mM phosphate, pH 7.4, 1% BSA, 0.9% NaCl and 0.1% Tween-20 were added and incubated for 30 min at 30° C. The excess of conjugate was removed by washing the plates three times with 0.9% NaCl, 0.1% Tween-20. The amount of bound conjugate was detected by incubation with 200 μl TMB solution (Roche Diagnostics GmbH, Penzberg, Germany, Catalog No. 12034425) for 15 min. The enzymatic reaction was stopped by the addition of 50 μl 1 M $H_2SO_4$. The color development was quantified at 450 nm using a ELISA reader. The concentration of ASC in a serum or plasma sample was calculated from the standard curve using a serial dilution of recombinant SlyD-ASC-His-fusion protein.

Example 5

Marker Evaluation, Sensitivity and Specificity; ROC Analysis to Assess Clinical Utility in Terms of Diagnostic Accuracy Accuracy is assessed by analyzing individual liquid samples obtained from well-characterized patient cohorts. The control collective (see Table 1) contains 234 females consisting of 172 blood donors and 62 patients having undergone mammography. These 62 patients are found mammography negative and no symptoms of other breast diseases are detected.

The 174 breast cancer patients were put together from patients with ductal, lobular, tubular, medullary and mucinous carcinomas of different stages. Due to the aim to diagnose breast cancer at early stages, the proportion of UICC I and UICC II stages was 80%. To analyze the specificity to other non-malignant breast diseases 77 different non-malignant breast and 9 non-malignant gynaecological diseases are included into the sample cohort. The cohort is summarized in Table 1.

CA 15-3 and CEA were measured by commercially available assays (Roche Diagnostics, CA 15-3-assay: Cat. No. 0 304 5838 and CEA-assay: Cat. No. 1731629) for Elecsys® Systems immunoassay analyzer) and ASC was measured as described above in a serum aliquot obtained from each of these individuals.

TABLE 1

| Patient Collective | | |
|---|---|---|
| Healthy patients Σ | | 234 |
| | Female blood donors (without mammography) | 172 |
| | Healthy females (mammography negative) | 62 |
| Breast cancer Σ | Stage | 174 |
| | UICC I | 71 |
| | UICC II | 68 |
| | UICC III | 25 |
| | UICC IV | 6 |
| | Without staging | 4 |
| Disease Controls Σ | | 86 |
| | Fibroadenoma | 20 |
| | Papilloma | 6 |
| | Papillomatose | 3 |
| | LCIS (lobular carcinoma in situ) | 2 |
| | Mastitis | 9 |
| | Microcalcification | 8 |
| | Fibrocistic Diseases | 23 |
| | Cysts | 4 |
| | Other breast diseases | 2 |
| | Gynaecological Disease Controls | 9 |

The cut-off is defined with respect to the 95% percentile of the healthy control group, equalling 95% specificity. Thus, in the present series of experiments the cut-off value for ASC is set to 0.60 ng/ml.

Looking at the disease control group the specificity of mammography is very low (18.2%). The advantage of a breast cancer marker is the higher specificity compared to mammography. Using the cut-off of 0.6 ng/ml, the specificity of ASC in the disease control group was determined with 68.6%, which is lower as for CA 15-3 or CEA. Due to the higher level of ASC in the disease control group compared to the healthy controls, there is a need to include disease controls in the determination of the cut-off concentration. But using this cut-off value in the breast cancer samples a sensitivity of 30.5% was achieved, which is higher than for the well-known markers CA 15-3 and CEA. There is also a very high detection rate of ASC in the early stages (see Table 2).

The data summarizing sensitivity and specificity of ASC in comparison to the markers CEA and CA 15-3 are given in Table 2 and Table 3.

TABLE 2

| | Sensitivity | | | |
|---|---|---|---|---|
| Number of positive results | Sample Number | ASC | CA 15-3 | CEA |
| UICC I | 71 | 18 | 8 | 12 |
| UICC II | 68 | 23 | 14 | 11 |
| UICC III | 25 | 9 | 12 | 8 |
| UICC IV | 6 | 2 | 2 | 3 |
| Without staging | 4 | 1 | 1 | 1 |
| Total | 174 | 53 | 37 | 35 |
| Sensitivity | — | 30.5% | 21.3% | 20.1% |

TABLE 3

| | Specificity | | |
|---|---|---|---|
| Values given in [%] | ASC | CA 15-3 | CEA |
| Healthy Controls | 94.4 | 91.0 | 92.3 |
| Disease Controls | 68.6 | 87.2 | 90.7 |

To see the differentiation power of a new marker without consideration of a cut-off value a ROC analysis was performed according to Zweig, M. H., and Campbell, supra. The Discriminatory power for differentiating patients in the breast cancer group from the "healthy" control group as measured by the area under the curve was 80% for ASC and better as compared to the established markers CA 15-3 (57%) and CEA (69%), respectively. If the disease controls were included into the "control" group, the area under the curve dropped to 72%, but was always higher than for CA 15-3 and CEA.

TABLE 4

| | ROC values | | |
|---|---|---|---|
| Values given in [%] | ASC | CA 15-3 | CEA |
| Breast cancer/healthy controls | 80 | 57 | 69 |
| Breast cancer/healthy controls + disease controls | 72 | 57 | 67 |

Since the sensitivity and specificity of a marker can easily be changed by shifting the cut-off value, the best tool to analyze the differentiation power of a new marker is the ROC analysis. Using this tool, ASC has the best discrimination power between breast cancer patients and control samples including other breast diseases compared to the well-known markers CA 15-3 and CEA. Furthermore, ASC is able to detect more tumors at early stages. Using all control samples including disease controls the discriminative power of ASC (72%) is higher than for CA 15-3 (57%) and CEA (67%). The data indicate that ASC may be very helpful in the diagnosis of breast cancer or in the follow-up of patients after surgery.

In some of the samples from BC patients both the levels of ASC as well as the level of CA 15-3 are elevated. In addition, either ASC or CA 15-3 is positive in individual samples obtained from different breast cancer patients. This leads to a higher sensitivity if both markers are measured in a patient sample. If a patient sample is classified as positive in case one of the markers ASC or CA 15-3 is positive, then a higher sensitivity can be achieved.

Preliminary data indicate that ASC may also be very helpful in the follow-up of patients after surgery.

What is claimed is:

1. A method for a diagnosis of breast cancer comprising the steps of:
   (a) providing a liquid sample obtained from an individual,
   (b) directly contacting the sample with an antibody specific for human apoptosis-associated speck-like protein containing a caspase-associated recruitment domain (ASC) under conditions whereby a complex is formed between the antibody and ASC and wherein the antibody has an affinity of at least $10^7$ l/mol for ASC,
   (c) measuring an amount of complex formed, and
   (d) comparing the amount of complex formed to a control amount determinative of the diagnosis of breast cancer, wherein the liquid sample is selected from the group consisting of serum, plasma, whole blood, and nipple aspirate fluid, and further wherein "directly" excludes contacting cellular and tissue samples separated from the liquid sample obtained in step (a).

2. The method according to claim 1 wherein the sample is serum.

3. The method according to claim 1 wherein the sample is plasma.

4. The method according to claim 1 wherein the sample is whole blood.

5. The method according to claim 1 wherein the sample is nipple aspirate fluid.

6. The method of claim 1 wherein the individual is a breast cancer patient in stage $T_{is}$-3; N0; M0.

7. The method of claim 1 wherein step (d) further includes comparing an amount of one or more markers in the sample selected from the group consisting of CA 15-3 and cellular retinoic acid-binding protein II to a control amount determinative of the diagnosis of breast cancer.

* * * * *

SEQUENCE LISTING

```
<160> NUMBER OF SEQ ID NOS: 5

<210> SEQ ID NO 1
<211> LENGTH: 195
<212> TYPE: PRT
<213> ORGANISM: Homo sapiens
<220> FEATURE:
<221> NAME/KEY: MISC_FEATURE
<223> OTHER INFORMATION: apoptosis-associated speck-like protein
      containing a CARD (ASC)

<400> SEQUENCE: 1

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
                20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
        195

<210> SEQ ID NO 2
<211> LENGTH: 53
<212> TYPE: DNA
<213> ORGANISM: Artificial sequence
<220> FEATURE:
<223> OTHER INFORMATION: primer 1 which is referred to in Example 1

<400> SEQUENCE: 2
atgcgaattc attaaagagg agaaattaac tatgaaagta gcaaaagacc tgg          53

<210> SEQ ID NO 3
<211> LENGTH: 61
<212> TYPE: DNA
<213> ORGANISM: Artificial sequence
<220> FEATURE:
<223> OTHER INFORMATION: primer 2 which is referred to in Example 2
```

-continued

```
<400> SEQUENCE: 3
gcatgagctc acggccttca ataccgccac cagagccacc gccggaaccg ccaccggatc    60
c                                                                   61

<210> SEQ ID NO 4
<211> LENGTH: 72
<212> TYPE: DNA
<213> ORGANISM: Artificial sequence
<220> FEATURE:
<223> OTHER INFORMATION: primer 3 which is referred to in Example 2

<400> SEQUENCE: 4
atgcggatcc ggtggcggtt ccggcggtgg ctctggtggc ggtattgaag gccgtgggcg    60
cgcgcgcgac gc                                                       72

<210> SEQ ID NO 5
<211> LENGTH: 65
<212> TYPE: DNA
<213> ORGANISM: Artificial sequence
<220> FEATURE:
<223> OTHER INFORMATION: primer 4 which is referred to in Example 2

<400> SEQUENCE: 5
gcataagctt tcattagtga tggtgatggt gatgggaacc gccaccgctc cgctccaggt    60
cctcc                                                               65
```